United States Patent [19]

Cannon

[11] 3,986,514

[45] Oct. 19, 1976

[54] BATTERY FOR USE WITH IMPLANTABLE HEART PACER

[75] Inventor: Robert Lee Cannon, Waltham, Mass.

[73] Assignee: American Optical Corporation, Southbridge, Mass.

[22] Filed: Dec. 22, 1975

[21] Appl. No.: 643,289

Related U.S. Application Data

[63] Continuation of Ser. No. 418,516, Nov. 23, 1976, abandoned.

[52] U.S. Cl. .......................... 128/419 PS; 429/163; 429/185
[51] Int. Cl.² ............................................. A61N 1/36
[58] Field of Search...... 128/419 P, 419 PG, 419 PS; 136/133, 166, 168

[56] References Cited
UNITED STATES PATENTS

| | | | |
|---|---|---|---|
| 2,143,245 | 1/1939 | Lines | 136/133 |
| 2,457,810 | 1/1949 | Ellis | 136/133 |
| 3,757,793 | 9/1973 | Fester et al. | 128/419 PS |
| 3,823,037 | 7/1974 | Cairns et al. | 128/419 PS |
| 3,906,959 | 9/1975 | Cannon | 128/419 P |

FOREIGN PATENTS OR APPLICATIONS

| | | | |
|---|---|---|---|
| 1,221,765 | 1/1960 | France | 136/133 |

*Primary Examiner*—William E. Kamm
*Attorney, Agent, or Firm*—Stephen A. Schneeberger; William C. Nealon; H. R. Berkenstock, Jr.

[57] ABSTRACT

An improved battery for use with an implantable heart pacer. An implantable heart pacer provides stimulation to the heart of a patient and is normally battery-powered. A primary reason for pacer failure and resulting pacer replacement is failure in the battery or batteries. The present invention provides improved insulation against leakage between positive and negative electrodes of the implanted battery thus extending battery life and pacer life.

6 Claims, 5 Drawing Figures

U.S. Patent  Oct. 19, 1976  3,986,514
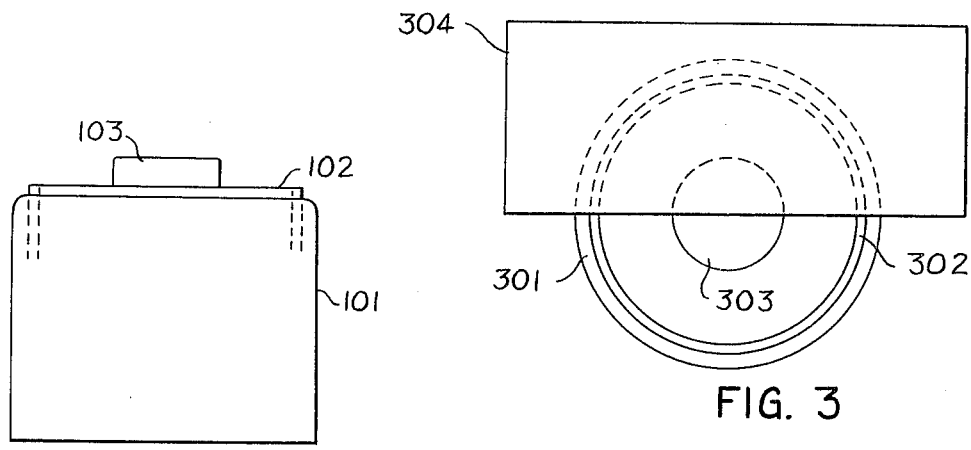
FIG. 1 PRIOR ART
FIG. 3
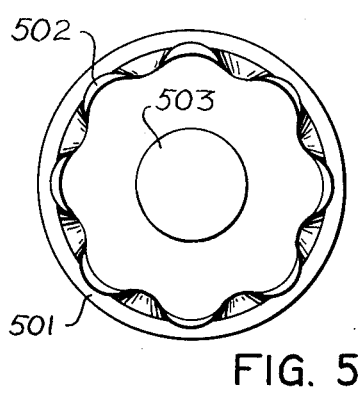
FIG. 5
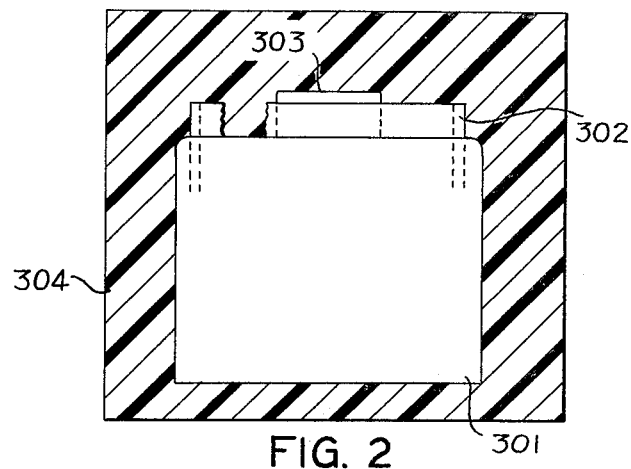
FIG. 2
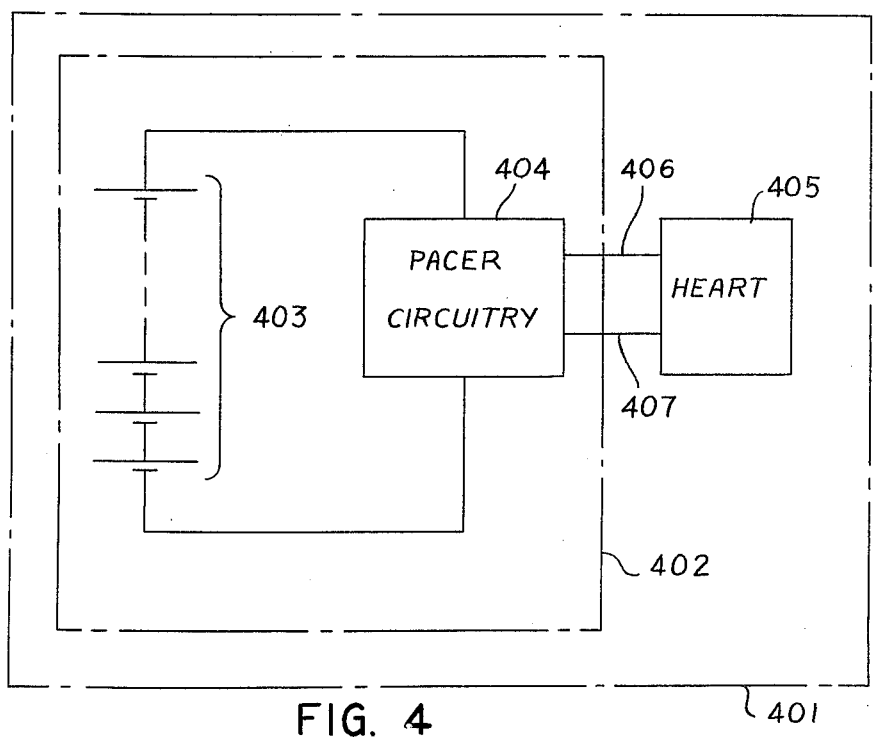
FIG. 4

BATTERY FOR USE WITH IMPLANTABLE HEART PACER

This is a continuation of application Ser. No. 418,516, filed Nov. 23, 1973, and now abandoned.

BACKGROUND OF THE INVENTION

1. Field of the Invention

The present invention relates in general to the field of medical-electronics. More particularly, the present invention relates to heart stimulating devices commonly known as heart pacers.

2. Description of Prior Art

Heart stimulating devices have been known for some time. Several years ago, heart stimulating devices which provide stimulation at a fixed or constant rate were developed. They were deficient since they created competitive problems with the natural or spontaneous heartbeat. More recently, heart stimulating devices which supply stimulation to the heart only when required have been developed, and these pacers solved the competition problem. And even more recently, heart pacers that supply stimulation only when required and in proper sequence to two chambers of the heart, the atrium and ventricle, have been developed.

In all pacers designed for use within the body of a patient whose heart is to be stimulated, a portable power supply is necessary. Ordinarily, a battery power supply is used, where it is desirable for battery life to be of long duration. For example, pacer batteries of chemical composition can be operative for as long as 2 years or more. More recently, nuclear batteries and other sources of circuitry energization have been developed. However, these newer methods of circuitry energization are attendant with certain severe technical problems which do not burden pacers powered or energized by conventional chemical batteries. But, chemical batteries have leakage problems to be described below.

A mercuric-oxide-zinc chemical composition is a typical chemical composition for a pacer battery. This battery is the type that requires venting of fluids as internal chemicals mutually react. The liquid which is vented or discharged from the battery is usually an aqueous solution of sodium hydroxide or potassium hydroxide. This aqueous solution of either of these electrolytes can provide an effective leakage conductive path for current flow between positive and negative electrodes of a battery cell. Alternatively, or additionally, water from regions external to the implanted pacer may seep into the pacer through various apertures, (for example, the aperture where the catheter inter-connects with the pacer circuitry), and may likewise electrically connect positive and negative electrodes of a battery cell causing a leakage path for that particular cell. Leakage current flow can substantially reduce effective life of a battery, and thus substantially reduce the pacer's life.

Approximately 70% of pacers that are presently being used fail due to battery exhaustion. Battery exhaustion, as earlier noted, is increased by leakage paths between positive and negative electrodes of individual battery cells. There is evidence which indicates that with regard to mercury battery cells, approximately half of the potential energy is utilized for productive work; therefore, it is possible that the other half of potential energy of the mercury cell is wasted in leakage currents across grommets of prior art design. The present invention is an improvement to conventional chemical batteries subject to this leakage problem. The present invention can extend battery life possibly up to 100%.

SUMMARY OF THE INVENTION

The present invention relates to an improvement in batteries used for powering implantable heart pacers. A grommet, which can be constructed from neoprene rubber, is located or inserted between positive and negative terminals of the battery. The grommet is designed to extend substantially beyond the surface enclosure of the battery for the purpose of providing substantial contact area between the neoprene surface and the epoxy which encapsulates both batteries and heart pacer circuitry. The improved bonding between epoxy and grommet forms a leak-proof covering over each electrode. Any liquid which forms in the area of the battery, as a result of external moisture seeping in or as a result of venting of the batteries themselves, will not provide a conductive path from one electrode to the other because of the barrier created by the bonding. In a particular embodiment of this invention, a fluted grommet is utilized to further improve bonding action between grommet and epoxy. It is an advantage of the present invention to substantially extend battery life and hence pacer operational life.

It is thus an object of this invention to provide an improved heart pacer.

It is another object of this inventon to provide an improved battery for use with a heart pacer.

It is yet another object of this invention to provide an improved battery which has a leak-proof covering over each of its electrodes.

BRIEF DESCRIPTION OF THE DRAWINGS

FIG. 1 depicts an elevational view of a prior art battery;

FIG. 2 depicts an elevational view of an illustrative embodiment of the present invention;

FIG. 3 depicts a top view of the illustrative embodiment of the present invention of FIG. 2;

FIG. 4 is an illustrative embodiment of an improved heart pacer utilizing the battery of the present invention; and FIG. 5 depicts a top view of an alternative embodiment of the present invention.

DESCRIPTION OF THE PREFERRED EMBODIMENTS

Referring to prior art FIG. 1 one can see that negative electrode 103 is separated from positive electrode 101 by grommet 102. The electrodes and grommet may have generally cylindrical shape and conform to each other in a concentric manner. However, grommet 102 extends above the exterior surface of the battery by only a small distance. This small distance does not permit sufficient surface area contact between the grommet walls and the encapsulating epoxy which is contiguous to the surface of this structure to form a leak-proof bond.

Note that the internal portion of grommet 102 is hidden from view by the outer surface electrode 101 and is thus partially shown by dashed lines. The shape of the grommet internal to the cell may deviate from a cylindrical shape; thus the dashed lines are not completely extended and are intended to represent the fact that a variety of shapes can be utilized. Since the present invention is located external to the battery, the actual detailed shape of the grommet internal to the cell is not necessary for complete understanding of the invention. Similarly, internal construction and layout of the positive and negative electrodes are also not detailed for the same reasons.

But, consider the illustrative embodiment of Applicant's invention in FIGS. 2 and 3 where negative electrode 303 is separated from positive electrode 301 by grommet 302 which is indicated to be substantially extended from the surface of the battery. (Again internal construction of the cell is not detailed since it is not necessary for complete understanding of the present invention.) Grommet 302 is selected to be non-conductive and to have the property of forming a leak-proof chemical bond with non-conductive, encapsulating epoxy 304. FIGS. 2 and 3 depict epoxy 304 encapsulating only half of the battery or cell for purposes of clarity of illustration. Grommet 302 can be formed from neoprene rubber, for example. It should be understood that grommet 302 can be extended to even further lengths, and can have other shapes providing even greater surface area contact, and is depicted with the particular size shown only for purposes of clarity of illustration. (An alternative embodiment is described below.)

Significantly increased surface contact area is achieved between grommet 302 and the surrounding epoxy. Epoxy 304 is contiguous with the exterior surface of the battery and grommet. This larger contact area results in a leak-proof bonding between epoxy and grommet. This bonding results in a leak-proof barrier or covering over each of the electrodes. The inside circumferential wall of the neoprene rubber grommet and the centrally-located epoxy form a covering over centrally located negative electrode 303. The outer periphery of the grommet and peripherally-located epoxy form a second covering over positive electrode 301.

It should be understood that venting of battery electrolytes described above creates high pressure. It is estimated that pressures on the order of thousands of sounds per square inch have developed in these pockets immediately external to the electrodes. In the event that pressure does get too high even for the improved bond of the present invention, the longer path length created by the larger grommet results in a higher resistance and a lower leakage rate in the event that conductive liquid does inter-connect the two electrodes. Consequently, the present invention solves the problem of pacers which fail due to an abrupt failure of one cell because of high leakage paths. It is estimated that 20% to 30% of pacers which fail have this failure mode.

Next, consider FIG. 4. FIG. 4 depicts heart pacer circuitry 404 being energized by batteries 403. The dashed line between individual cells of batteries 403 is intended to indicate that more or less than the number of batteries illustrated can be used. Boundary 402 is intended to represent the outer surface of the epoxy encapsulation described above. It is the bonding between this epoxy and the grommet 302 (not shown in FIG. 4) which creates the improved bonding that results in extended battery life. Patient's heart 405 is illustrated to be located external to the epoxy shield and electrically connected to the pacer circuitry by terminals 406 and 407. Boundary 401 is intended to represent skin surface of the patient in whom the epoxy encapsulated pacer system is implanted.

It is to be understood that almost any pacer circuitry that is adaptable for use in the manner herein described can be powered by these improved batteries. To this end, background material and circuitry described in U.S. Pat. Nos. 3,528,428 and 3,595,242 are hereby incorporated by reference, since these patents, among others, describe heart pacers that are suitable use with these improved battery cells.

FIG. 5 illustrates an alternative embodiment of the present invention. Negative electrode 503 is separated from positive electrode 501 by fluted grommet 502. This fluted design permits more surface area contact between grommet and epoxy than is available by the cylindrically-shaped grommet of FIG. 2, for a given maximum extension of the grommet from the exterior surface of the battery.

The invention may be embodied in yet other specific forms without departing from the spirit or essential characteristics thereof. For example, an external, portable pacer may likewise have batteries of the present invention. Thus, the present embodiments are to be considered in all respects as illustrative and not restrictive, the scope of the invention being indicated by the appended claims rather than by the foregoing description, and all changes which come within the meaning and range of equivalency of the claims are therefore intended to be embraced therein.

What I claim is:

1. A heart pacer for providing stimulation to the heart of a patient, said pacer comprising terminal means for connection to said heart, pulse generator means for providing stimulation impulses on said terminal means at predictable interimpulse intervals, battery means for energizing said pulse generator means, insulation encapsulating said battery means and said pulse generator means, said battery means comprising an exterior multi-surfaced battery housing, positive and negative electrodes, all but one surface of said housing being employed as one of said electrodes, the other of said electrodes extending from a central portion of said one surface for a predetermined distance, and insulating grommet means located between said electrodes in mutually insulating engagement therewith and having an exterior surface in bonded contact with said insulation, the area of said grommet means exterior surface in said bonded contact with said insulation being at least sufficient to provide substantially leak-proof coverings over each of said positive and negative electrodes thereby to mutually insulate said positive and negative electrodes externally of said battery housing and said grommet means.

2. A pacer as recited in claim 1 and wherein said insulation is epoxy.

3. A pacer as recited in claim 1 and wherein said grommet means is constructed from neoprene.

4. A pacer as recited in claim 1 and wherein said battery means is a battery having a mercuric-oxide-zinc chemical composition.

5. A pacer as recited in claim 4 and wherein one of said electrodes and said grommet are concentric cylinders centered about the other of said electrodes in the region in which it makes contact with said insulation.

6. A pacer as recited in claim 5 and wherein said grommet is constructed to have fluted surface in the region in which it makes contact with said insulation.

* * * * *